United States Patent [19]
Katz

[11] Patent Number: 6,027,478
[45] Date of Patent: Feb. 22, 2000

[54] NASAL CAVITY DRAINAGE AND STOPPAGE SYSTEM

[75] Inventor: Warren Katz, Dallas, Tex.

[73] Assignee: Medical Purchasing Group, Inc., Dallas, Tex.

[21] Appl. No.: 08/947,577

[22] Filed: Oct. 9, 1997

[51] Int. Cl.$^7$ .................................................. A61M 29/00
[52] U.S. Cl. ........................... 604/102; 604/96; 606/196; 606/199
[58] Field of Search ................................... 604/35, 49, 54, 604/94, 96, 102, 275, 276; 606/192, 194, 196, 199

[56] References Cited

U.S. PATENT DOCUMENTS

| | | |
|---|---|---|
| 2,493,326 | 1/1950 | Trinder . |
| 2,847,997 | 8/1958 | Tibone . |
| 3,766,924 | 10/1973 | Pidgeon . |
| 3,850,176 | 11/1974 | Gottschalk . |
| 3,903,893 | 9/1975 | Scheer . |
| 4,180,076 | 12/1979 | Betancourt ............................... 604/102 |
| 4,729,384 | 3/1988 | Bazenet .................................... 128/691 |
| 5,139,510 | 8/1992 | Goldsmith, III et al. . |
| 5,477,852 | 12/1995 | Landis et al. ....................... 128/207.18 |
| 5,725,496 | 3/1998 | Peters ......................................... 604/49 |
| 5,746,717 | 5/1998 | Aigner ..................................... 604/102 |
| 5,797,877 | 8/1998 | Hamilton et al. .......................... 604/96 |

OTHER PUBLICATIONS

Controlling Intraoperative and Postoperative Nasal Bleeding, Stewart D. Fordham, M.D., *Plastic and Reconstructive Surgery*, vol. 90, No. 5, Nov. 1992.

Micromedics, Inc. brochure describing RhinoCath™ Nasal Catheter, ® Micromedics, Inc. 1996, 1997.

*Primary Examiner*—Wynn Wood Coggins
*Assistant Examiner*—LoAn H. Thanh
*Attorney, Agent, or Firm*—Sanford E. Warren, Jr.; Gardere & Wynne, L.L.P.

[57] ABSTRACT

A method for simultaneously isolating the flow of blood in a nasal cavity and withdrawing the blood from the nasal cavity is disclosed. The method comprises the steps of inserting a catheter into the nasal cavity. The catheter is composed of a tube and a duct and a forward end capable of being enlarged to form a balloon. Once the catheter is positioned in the nasal passage, air is pumped into the catheter through the tube to inflate the balloon. The inflated balloon forms a seal within the nasal cavity that prevents the flow of blood beyond the seal.

Simultaneously, blood is drawn into the catheter by applying a suction force to the duct. Suction may be accomplished by attaching a vacuum at the opposite end of the catheter and connecting it to the duct. The blood is drawn into the duct through a plurality of holes that connect the periphery of the catheter with the duct. The blood thus drawn into the duct is removed from the nasal cavity and disposed away from it.

6 Claims, 4 Drawing Sheets

NASAL CAVITY DRAINAGE AND STOPPAGE SYSTEM

TECHNICAL FIELD OF THE INVENTION

The present invention relates in general to the field of nasal surgery and more specifically to a method and apparatus for the removal of blood during nasal septal reconstructive surgery and stoppage of blood from the nasal cavity to the throat.

BACKGROUND OF THE INVENTION

Nasal septal reconstructive surgery has many facets. Often it will involve autogenous cartilage drafting and external nasal reconstruction. This is accomplished by going inside the nasal cavity and cutting and removing tissues as part of the reconstructive activity. This type of surgery has several inherent features that impede a physician's ability to perform the procedure. Obviously during the course of the operation, the procedure for nasal reconstructive surgery causes a flow of blood both into and out of the nasal cavity.

The flow of blood during nasal septal reconstruction creates several difficulties associated with the procedure. The blood flows into the nasal cavity in two different directions, both deeper into the nasal cavity from the point of laceration and, in the opposite direction, out of the patients nose. Blood flowing further into the nasal cavity causes choking action and breathing difficulties on the part of the patient which in turn triggers certain autonomic reflexes that are potentially hazardous and can otherwise be obstructive to the patient's well being. Blood flowing forward can obviously be an obstruction to the physician's ability to perform the surgery.

Another solution to the problem of blood flow during nasal septal reconstruction has been the use of a nasal tampon designed to control nasal hemorrhage. Unfortunately, the nasal tampon requires the use of an absorptive sponge that must be moistened prior to insertion. The sponge portion of the nasal tampon must also be compressed prior to insertion, and regains its sh ape as the tampon portion is being inserted, causing abrasions to the inner surfaces to the nose. Finally, the nasal tampon only serves to remove blood from the area and has no control capabilities as to the extent of pressure on the walls of the nasal cavity or the amount of damage that can happen during its retraction.

Therefore, what is needed is a method for simultaneously blocking the flow of blood from going further into the patient's nasal cavity while withdrawing blood flowing in the opposite direction. By performing these two steps simultaneously the physician reduces the likelihood of the patient suffering breathing and choking difficulties caused by the flow of blood and prevents the blood flowing out the patient's nose from obstructing the procedure being performed by the physician.

In the past physicians primarily used gauze to remedy the problem of blood draining out of the nasal cavity. A physician would pack the gauze into the nasal cavity. The gauze was used to absorb the flow of blood. This would help reduce the blood's interference with the physician's operation. However, the use of gauze in nasal septal reconstruction created other problems.

First, the use of gauze had certain limitations. Depending on the size of the surgery, one may not be able to utilize enough gauze to stop the flow of blood because the physician needs space to operate. In addition, gauze does not fully contain the flow of blood in all procedures. This means the physician has to change the gauze several times during the operation. This need to change gauze during a procedure interferes with the operation and increases the time the patient is under anesthesia. It is desirable to limit the time a patient is under anesthesia to as short a time as possible. Yet another limitation involved another type of interference. In using gauze as a sponge, the gauze would be placed in the nasal cavity during the operation and removed afterward. Often times it was found that when the gauze was removed after an operation some of the reconstructed tissue would deform. This is because it had been supported by the gauze during the reconstruction. This created the need to repeat the reconstructive procedure, reinforcing work that had already been done, so that it could exist independently of the support of the gauze. Other than attempting to be more skilled at recognizing the problem, there was little a physician could do to alleviate it. There were various attempts but none that offer the benefits of the instant invention.

SUMMARY OF THE INVENTION

The invention provides a way to prevent the flow of blood deeper into a nasal cavity while simultaneously, quickly and non-obstructively removing the blood flowing out of the nasal cavity toward the exterior of the patient's nose. This is accomplished by inserting a catheter having an inflatable balloon at a forward end into the nasal cavity. Once inserted, inflating the balloon to seal off the rear portion of the nasal cavity. Blood is then suctioned out of the forward portion of the nasal cavity through a series of holes in the catheter and into an interior duct for quick and efficient removal.

The catheter is constructed of an outer tube, an inner duct and a plurality of holes that connect the duct with the outer surface of the tube. Inside the tube is a lumen used for transporting a substance, such as gas or liquid, into the balloon. The substance is used to inflate the balloon from a remote location. Blood is drawn into the duct while the balloon seals the nasal cavity, preventing any flow of blood further into the cavity.

In one embodiment the catheter is made of an elastomeric material. The material would have qualities that allow flexibility and strength. In addition it must have smooth surfaces, both inside and outside. The inner surface of the duct must be smooth so that blood can flow through it to be carried away from the nose.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which.

DETAILED DESCRIPTION OF THE INVENTION

The invention disclosed is for a method and apparatus for simultaneously isolating the flow of blood in a nasal cavity and withdrawing the blood from a nasal cavity. A catheter having a balloon near one end and two channels contained inside is inserted into a nasal cavity. The first channel forms a lumen for the flow of a liquid to inflate the balloon. Once properly in place, the balloon is inflated to form a seal with the cavity wall. The catheter has a plurality of holes in it. The holes lead to the inner channel, or duct. Blood is drawn into the duct through the holes and in this way is removed from the body.

Figure 1:
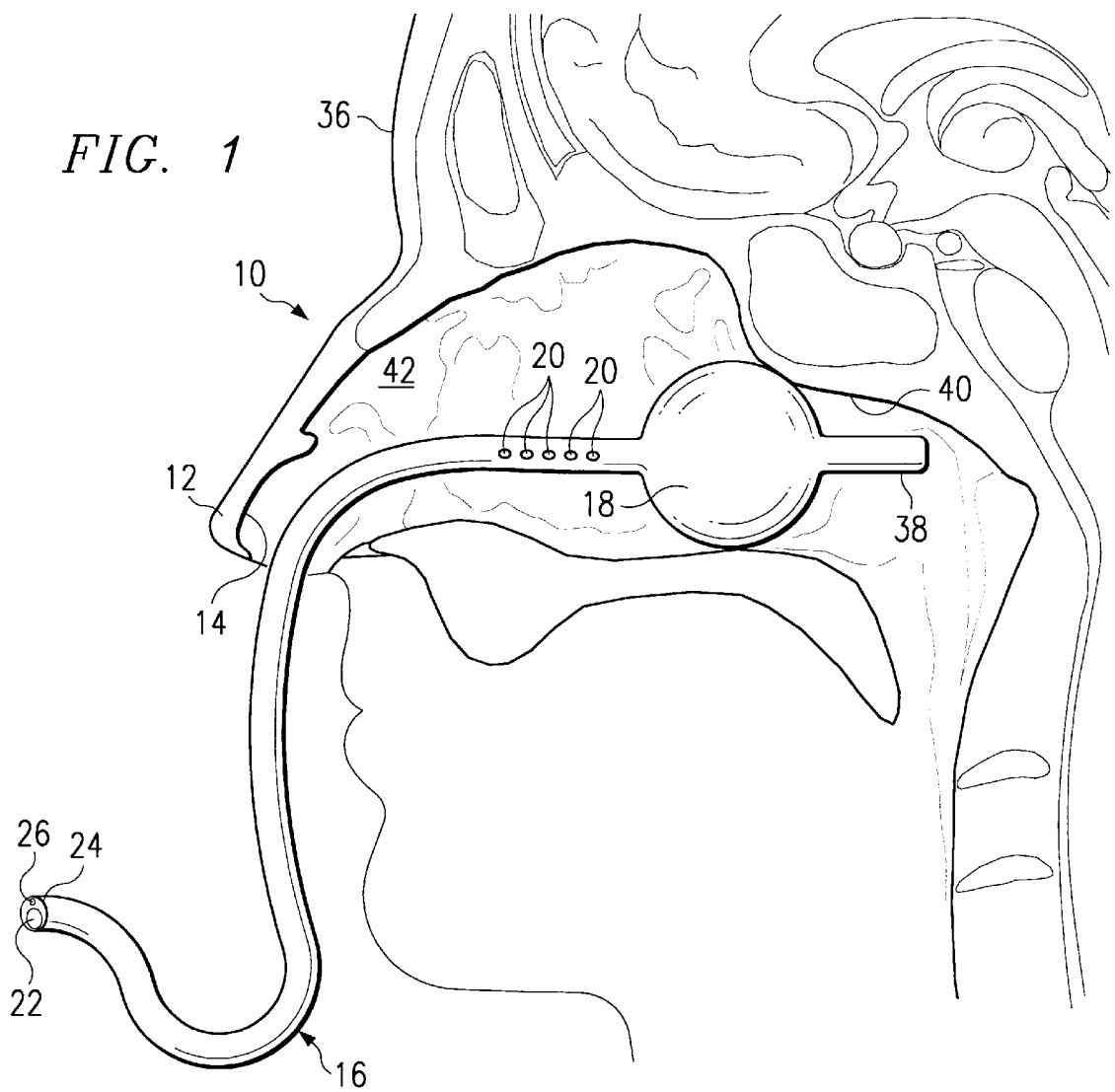
FIG. 1 illustrates a cutaway view of a human head with a catheter inserted therein.

In one embodiment of the invention is shown in FIG. 1. The illustration 10 shows a cutaway of a human head 36. Head 36 has a nose 12 having a nasal cavity 14. It may be seen from FIG. 1 that nasal cavity 14 is characterized by a tubular shape that extends from a rear portion 42 of nasal cavity to a forward portion 40 for purposes of our illustration. The tubular shape of nasal cavity 14 is irregular and varies in diameter at different points. The shape of nasal cavity 14 varies in diameter within a given head but also varies from head to head. Each nasal cavity 14 has a distinct shape. That shape is dictated by the individual's genetic code and any direct physical changes that may have occurred. Examples of such cavity 14 shaping events would include prior surgical operations or physical mishaps, such as sports injuries, that directly affect the shape of nasal cavity 14. This factor is important when choosing a method to stem the flow of blood in nasal cavity 14 while simultaneously removing the flowing blood from nasal cavity 14.

Inside nasal cavity 14 is a catheter 16. A catheter, being a slender, flexible tube that is inserted into the body, comes in a variety of shapes and sizes depending upon its specific purpose. In the present invention catheter 16 has unique features that are key to the invention. Overall, catheter 16 is slender, flexible and is inserted into the human body, see FIG. 1. It is slender enough so that it may be slidably inserted into a nasal cavity 14. This means that the diameter of catheter 16 must be small. It must also be long so as to be able to be connected to other devices outside of nasal cavity 14. The exterior of catheter 16 must be smooth and composed of such a material that ease of entry into nasal cavity 14 is enhanced by the surface contact. There are several potential materials catheter 16 may be made from, silicon, natural or synthetic rubber, polymer and elastomeric polymers. Combinations of all of these are well known in the art. They may be used to create an exterior surface that will facilitate the ease of entry of a catheter 16 into nasal cavity 14.

Figure 2:
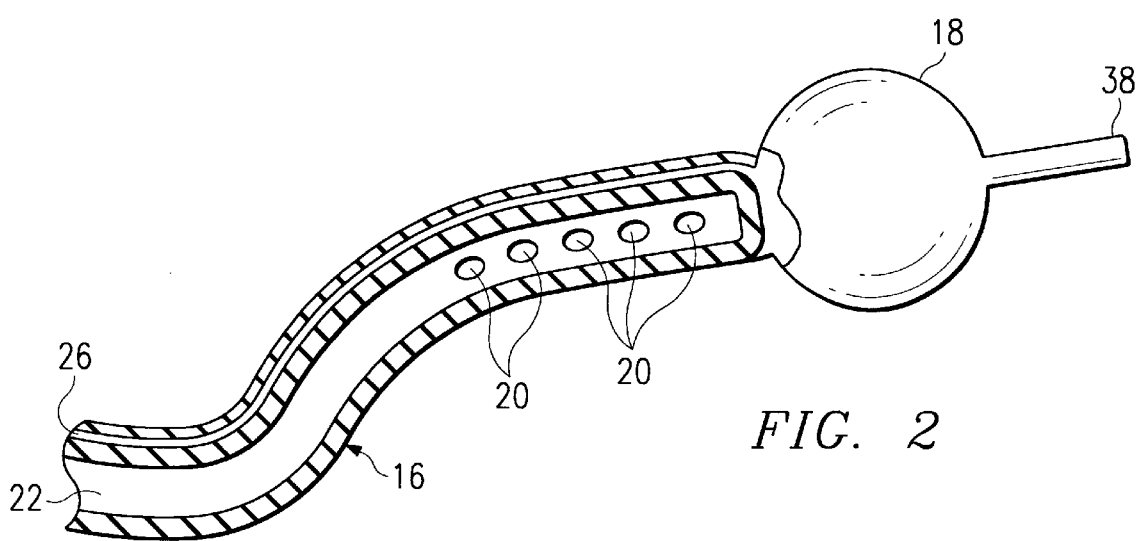
FIG. 2 shows a cutaway view of the invention.

Catheter 16, illustrated in FIG. 2 is composed of a tube 24 having an external surface area which makes up catheters' 16 outer surface and an internal surface area that forms the interior of the tube 24. The interior of tube 24 forms a duct 22. The duct 22 must also be made of a material having a smooth surface. A smooth surface will aid the passage of blood through duct 22 to a point of ultimate disposal. Duct 22 will generally be cylindrical in shape and have a large enough diameter to allow the flow of blood. Duct 22 is for most of its length coextensive with tube 24 and is used to transport blood, and potentially other bodily fluids, from one end of catheter 16 to another. Duct 22 is defined by an exterior surface that is also generally coextensive with the interior surface of tube 24 but spaced apart from tube's 24 interior surface.

Figure 7:
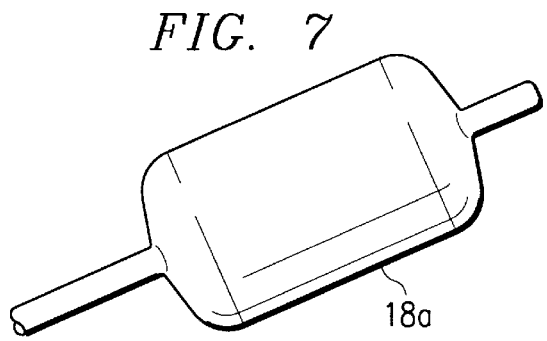
FIG. 7 shows a balloon in one embodiment.
Figure 8:
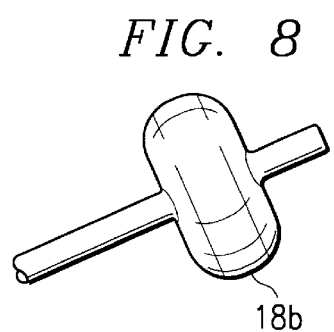
FIG. 8 shows a balloon in an alternative embodiment.
Figure 9:
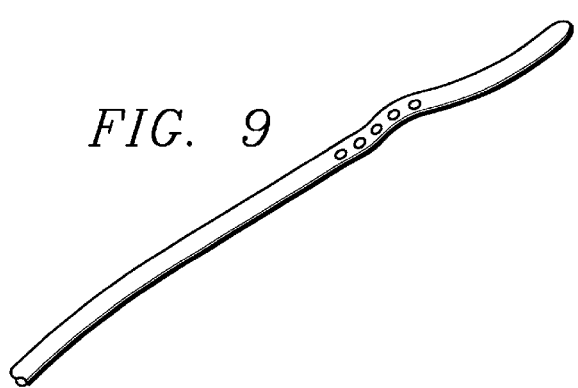
FIG. 9 shows a portion of a catheter having a non-inflated balloon.

FIG. 2 shows a view of catheter 16 outside of nasal cavity 14. It is a cutaway view of catheter 16 and all the components that it consist of. FIG. 2 provides a cutaway view of the internal as well as external structure. Catheter 16 shows a balloon 18 in its inflated state. The balloon 18 may be formed of a part of catheter 16 that has certain elastic properties that are not found in the rest of catheter 16. These properties would include the ability to deform and then return to its original shape. This may be accomplished by mechanically attaching a different type of material at the point where balloon 18 is to be placed. The recommended material would be more elastic and have the capability of being inflated. In addition, once inflated it must have enough elasticity to return to its original shape with little or no distortion from the initial shape. The more elastic material will inflate when put under pressure before the rest of tube 24. Another way to accomplish the construction of balloon 18 is to have a thinner diameter at the point where balloon 18 is to be located. The thinner diameter must be of sufficient diameter to not tear when placed under pressure, such as when in an inflated state. The length of balloon 18 is also a factor that must be considered. In FIGS. 7 and 8 other potential balloon 18 shapes are disclosed. FIG. 7 shows an elongated balloon 18a structure. This structure may be used to seal surface areas that are irregular and may not be engaged at a more narrow juncture. FIG. 8 shows a shortened balloon 18b. This structure may be used in places where nasal cavity 14 is convoluted and/or congested and there is not enough room for larger sized balloons 18. Obviously the size of balloon 18 depends on several factors. These factors include the size of nasal cavity 14, the amount of space within cavity 14, the types of obstructions that may be found inside nasal cavity 14 and the other geometry specific considerations. The factors for the shape of balloon 18 should also include take into consideration the properties of the material(s) that will be used to construct balloon 18. The physical properties may dictate to a certain degree the extent to which balloon 18 may be inflated and deflated and over what surface area.

Balloon 18 is inserted into a nasal cavity 14 in it's rest position, or deflated state. Once positioned, balloon 18 is then inflated so as to expand and engage the interior walls of nasal cavity 14. Balloon 18 is expanded until it is sealably engaged with nasal cavity 14 walls so as to prevent the flow of blood from the operating area to the forward portion 40 of nasal cavity 14 and into the patient. Balloon 18, when inflated, will assume a shape that will generally conform to the contours of the interior of nasal cavity 14. Catheter 16 is connected to a device that is used for drawing blood through holes 20 into duct 22 and out of nasal cavity 14, as herein described.

Figure 4:
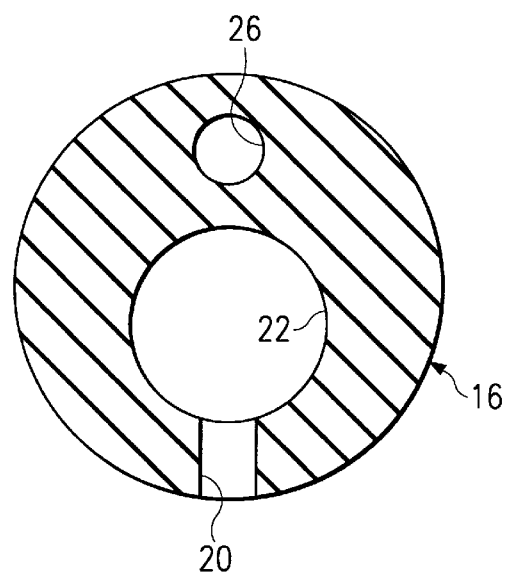
FIG. 4 shows a cross section of a catheter.
Figure 5:
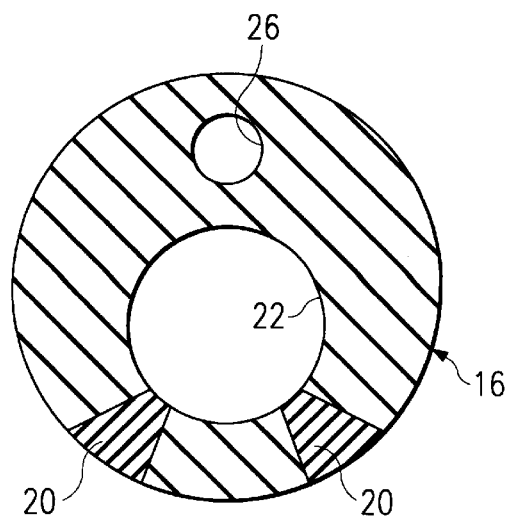
FIG. 5 shows a cross section of a catheter.
Figure 6:
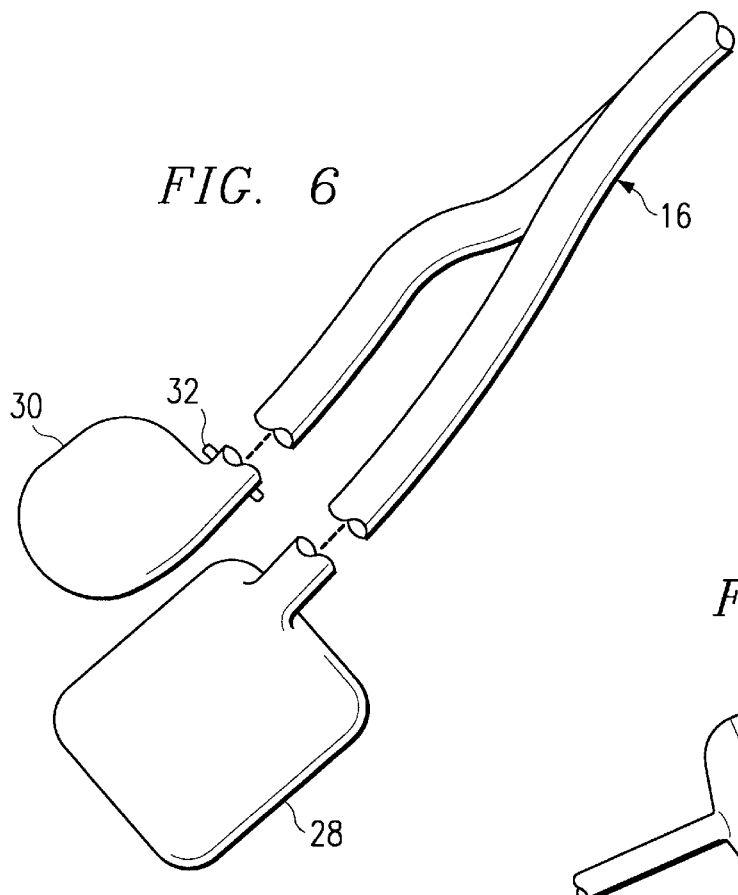
FIG. 6 illustrates a portion of a catheter attached to a pump and a suction device.

FIGS. 2, 4 and 5 disclose a lumen 26. Lumen 26 is contained entirely within the interior of tube 24. Lumen 26 in the embodiment described herein is completely contained within the interior of tube 24. It consist of a cylindrical shape whose external walls are coextensive throughout most of catheter 16 with the interior walls of tube 24. It can be seen from FIG. 2 that lumen 26 is coaxially aligned with catheter 16 for a portion of its length. The extent to which the two are coextensive depends upon a number of factors, including the types of devices attached to catheter 16 and the functional requirements of catheter 16. For example, the pumping device 30 that is attached to lumen 26 may have physical characteristics that cause it to severely lose pressure per unit length of lumen 26. In that situation, it would be desirable to have as short of a lumen 26 as possible. This would mean lumen 26 may be shorter in length than duct 22. Again, depending on the type of equipment that may be used, the opposite may be true. In general, lumen 26 and duct 22 are fairly coextensive except for slight differences dictated by operational needs.

FIGS. 4 and 5 show two different configurations of the physical relationship between holes 20, duct 22 and lumen 26. In both embodiments, lumen 26 and duct 22 are coexistent. It is through lumen 26 that a substance, gas or liquid, is pumped. In the invention described herein, water is the substance that is used. The water in turn inflates and deflates balloon 18 according to the needs of the physician.

FIG. 4 shows a dissectional cross view of catheter 16 having a lumen 26 within the interior of tube 24 at a particular portion. This configuration essentially places a pipe shaped lumen 26 inside the interior of tube 24. The remaining channel in the tube 24 serves as duct 22 to be used for the removal of the flow of blood from nasal cavity 14. There is one hole 20 placed opposite lumen 26.

FIG. 5 shows a dissectional cross view of catheter 16 having a tube 24 and a lumen 26 that is circumferentially coextensive with tube 24. In this embodiment lumen 26 is composed of space created between the exterior wall of a duct 22 and the interior wall of a tube 24. Here, there are two holes 20, in the same plane, at angles to lumen 26.

Returning to FIG. 2, the physical relationship between a balloon 18 and a lumen 26 is also disclosed. Balloon 18 is the terminal point for lumen 26. In the most general designs, duct 22 terminates at a point near balloon 18 allowing the passage that defined lumen 26, between duct 22 and the wall of tube 24, to expand and open into balloon 18. Duct 22 closes upon itself in a completely sealed fashion at this end of catheter 16 so that it does not extend into balloon 18. One purpose of this seal is to insure that any blood that enters duct 22 flows in only one direction. This necessarily means that the space that previously defined lumen 26 now empties into balloon 18. The terminal point for this space may be nipple 38, after having passed through balloon 18. This is clearly illustrated in FIG. 2. In an alternative form, the termination of the space may be the end of balloon 18.

FIGS. 3, 4, 5 and 9 illustrate various placements of a plurality of holes 20 at the distal end of catheter 16. In all the embodiments the plurality of holes 20 go through the outer surface of catheter 16, through the inner surface of catheter 16 and connects through to duct 22. It is through these holes 20 that blood is drawn and passes through associated duct 22 and out to a point removed from nasal cavity 14.

FIGS. 4 and 5 show holes 20 in different configurations in cross sectional views. In the cross sectional view, FIG. 4 shows a single hole 20. Holes 20 in this embodiment feed directly into a duct 22, thus providing for transport of a patient's blood from the nasal cavity 14 to said duct 22.

FIG. 5 discloses holes as being circumferentially displaced along the axis of catheter 16. They are open at the exterior surface of a tube 24, pass through tube 24 and through the interior surface of tube 24. From there holes 20 pass through the interior walls of tube and continue on, defined by a cylindrically enclosed space, into the exterior surface of duct 22, through to the interior surface. It is at this point that blood flowing into duct 22 joins the stream of blood that is being directed to a rear position for disposal. Holes 20 may be placed in an infinite number of arrangements and sizes. These are but two examples.

Figure 3:
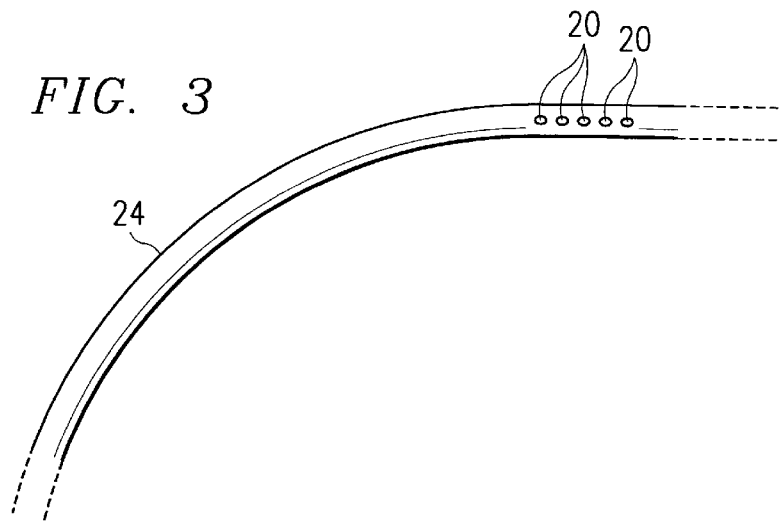
FIG. 3 illustrates a plurality of holes in a portion of a catheter.

FIG. 3 shows an embodiment wherein holes 20 are linear spaced in the direction of the length of catheter 16. FIG. 3 provides another illustration of plurality of holes 20. The placement of holes 20 in a tube 24 depends upon a number of different factors. Holes 20 must be positioned so as to enable blood withdrawal from within nasal cavity 14. One consideration in the placement of holes 20 is the desire to maximize holes' 20 ability to keep up with the rate of blood flow stemming from a patient's nasal cavity 16. If the type of surgery to be performed anticipates the need to remove an abnormally high flow of blood, there will be a need to increase either the number of holes or the size of the holes. The working requirements of suctioning device 28 to be attached would also be a consideration. The drawing power of suctioning device would dictate the number of openings. Another consideration would need to be the structural integrity of tube 24. It is desirable to avoid having so many holes 20 that tube 24 becomes structurally weakened. Other factors to be considered include the type of the material used to make tube 24, the number of holes 20 that are desired for the particular job and the type of device that will be used with catheter 16 to bring the blood into duct 22 through holes 20. The size of holes 20 will also be determined by these factors. Five (5) holes 20 are illustrated in FIGS. 2 and 3. In the one embodiment, holes 20 are equally spaced.

Figure 11:
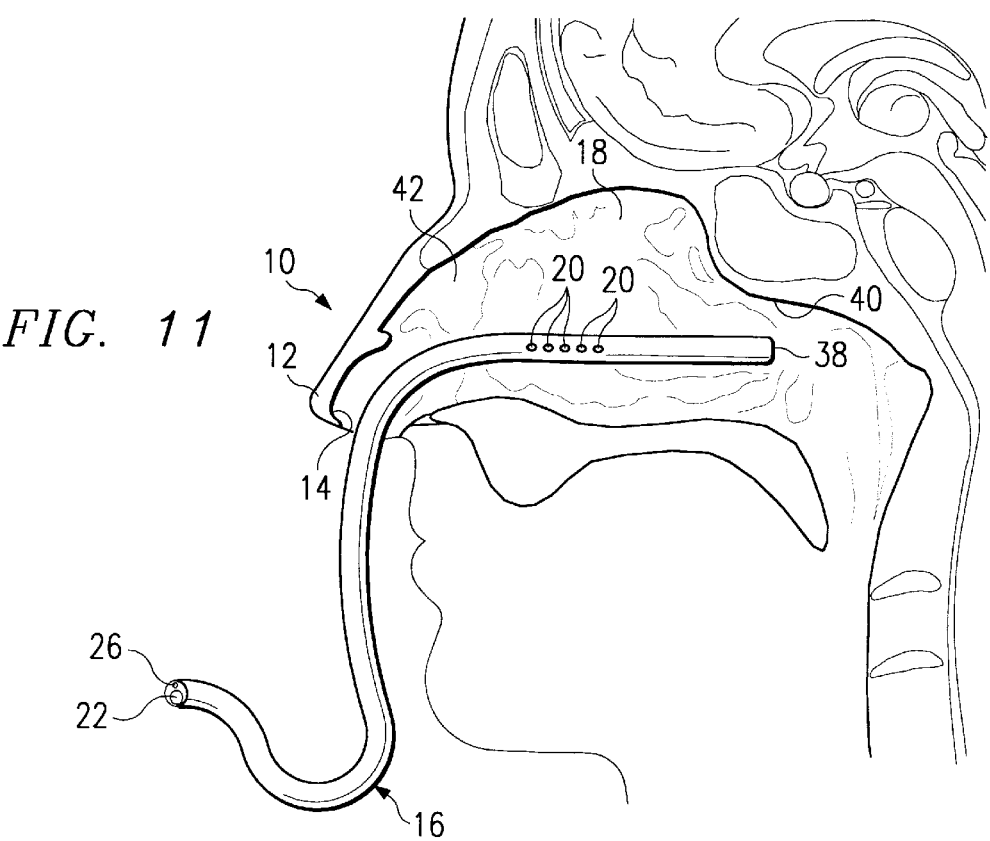
FIG. 11 shows the catheter inserted in a nasal cavity.

Nipple 38 is located at a far end of catheter 16 followed by an inflatable balloon 18 in its inflated state. Balloon 18 is slidably inserted into a nasal cavity 14 at a forward portion 40 of nasal cavity 14 as shown in FIG. 11.

Balloon 18 is followed by a plurality of holes 20 that go through outer tube 24 of catheter 16. Holes 20 lead to a duct 22 within catheter 16. The holes 20 are used to remove blood from the rear portion 42 of nasal cavity 14. This is accomplished by coercing the blood into holes 20 and into duct 22.

One form of coercion is to apply a suction force at the opening of holes 20 to draw the blood into duct 22. This may be accomplished by attaching a suctioning device to duct 22. This creates a suction force at the entrance of holes 20 . This suction would draw blood into duct 22 through holes 20. The suction force created by suction device 28 is spread out over the area of holes 20. In this way the blood is disposed quickly and effectively by being drawn into duct 22 as a result of the suction force at holes 20. The suction force should be sufficient to not only draw blood from an external source and into duct 22, but to also be able to be able to draw the blood along duct 22 unto it reaches a point where it will be disposed. This suction action should also be sufficient to overcome any obstructions that may occur. It is important that the suction force that is applied is not overly strong. If the force is too strong it will be hazardous to the surgery by drawing in, or at least pulling at, tissues that may become loosed during the procedure. This would exacerbate the work done by the physician because the placement of tissue, before, during and after an operation, is crucial.

Balloon 18 may be inflated by a pumping device, as shown at 30. The pumping device 30 must have the ability to inflate and deflate balloon 18 via the use of some substance that has the capability of flowing through lumen 26. As mentioned above, balloon 18 may be inflated by a gas or a liquid. The preferred embodiment would inflate balloon 18 with a gas because it is lighter than liquids. Air is a natural choice because of its availability. The pump 30 may have an associated device 32, or cut off valve, that can be releasably engaged allowing the user to either inflate or deflate balloon at will. Cutoff valve 32 is in an open position to allow gases or liquids to flow in or out and in the closed position to maintain gas in lumen 26 and balloon 18 at a desired pressure. Pump 30 should allow for variable control over the inflation pressure so that balloon 18 may expand only as much as needed and not cause any undue pressure in nasal cavity 14.

Figure 10:
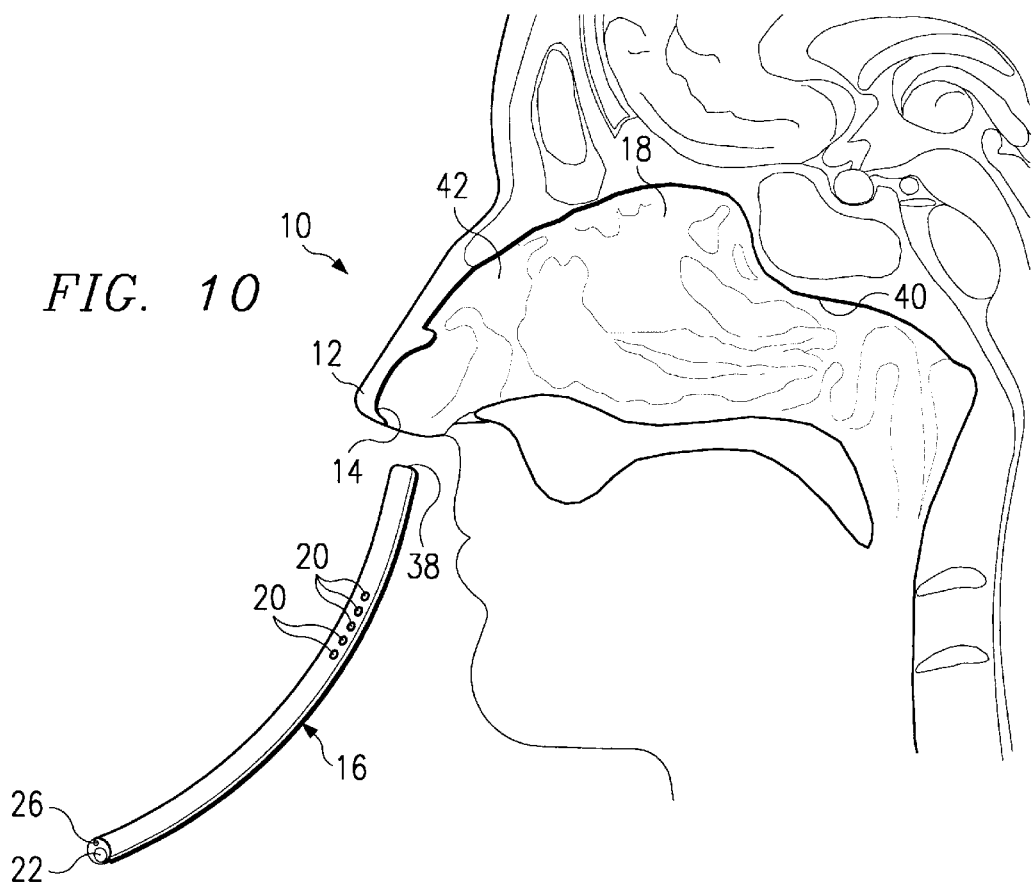
FIG. 10 shows a portion of the catheter prior to insertion.

In combination, a catheter 16 is slidably inserted into a nasal cavity 14, as illustrated in FIG. 10. Once positioned, a pumping device 30 is used to inflate a balloon 18 on catheter 16. A balloon 18 is inflated to engage the side walls of cavity 14. A suctioning device 28 attached to another end of catheter 16 is then activated creating a suction force within a duct 22 inside said catheter 16. The suction force is dispersed in duct 22 and applied at the openings of holes 20. Blood is suctioned into holes 20 and into duct 22 to be disposed of at a distant end. The physician then performs nasal reconstructive surgery relatively free of the flow of blood in either direction in nasal cavity 14.

After the operation is completed, balloon 18 is deflated. The entire catheter is then removed from nasal cavity 14.

While this invention has been described with reference to illustrative embodiments, this description is not intended to be construed in a limiting sense. Various modifications and combinations of the illustrative embodiments as well as other embodiments of the invention will be apparent to persons skilled in the art upon reference to the description. It 15 , therefore, intended that the appended claims encompass any such modifications or embodiments.

What is claimed is:

1. A method for simultaneously isolating the flow of blood in a nasal cavity and withdrawing the blood from the nasal cavity, comprising the steps of:

inserting a catheter having a tube and a duct in said nasal cavity;

inflating a balloon located near a forward end of the tube to form a seal within said nasal cavity; and withdrawing blood from within said nasal cavity through at least one hole in the periphery of said tube into said duct without disturbing the surrounding nasal cavity.

2. The method of claim 1, further comprising said withdrawal being a suctioning of said blood through said duct.

3. The method of claim 2, further comprising said withdrawing blood into said duct through plurality of holes disposed about said catheter.

4. The method of claim 1, further comprising:

deflating said balloon, and withdrawing said catheter from the nasal cavity.

5. The method of claim 3, further comprising said balloon returning to its original shape after being deflated.

6. The method of claim 1, further comprising withdrawing said blood through a plurality of holes.

* * * * *